United States Patent [19]

Fujita et al.

[11] 4,305,958
[45] Dec. 15, 1981

[54] CYSTEINE DERIVATIVES

[75] Inventors: Tadashi Fujita, Sakai; Masayuki Oya, Osaka; Hideo Takashina, Kobe; Tadashi Iso, Tondabayashi, all of Japan

[73] Assignee: Santen Pharmaceutical Co., Ltd., Osaka, Japan

[21] Appl. No.: 771,743

[22] Filed: Feb. 24, 1977

[30] Foreign Application Priority Data

Mar. 8, 1976 [JP] Japan .................................. 51-25455

[51] Int. Cl.$^3$ ................ C07C 149/243; A61K 31/195; C07C 149/247
[52] U.S. Cl. .................................... 424/319; 562/557; 562/426
[58] Field of Search .................... 260/534 S; 424/319; 562/557

[56] References Cited

U.S. PATENT DOCUMENTS

| 2,900,375 | 8/1959 | Amiard | 260/534 S |
| 3,246,025 | 4/1966 | Mita | 260/534 S |
| 3,647,834 | 3/1972 | Martin | 260/534 S |
| 4,053,651 | 10/1977 | Ondetti | 260/534 S |

FOREIGN PATENT DOCUMENTS 1491204 7/1967 France .............................. 260/534 S Primary Examiner—Natalie Trousof
Assistant Examiner—Michael Shippen
Attorney, Agent, or Firm—Frishauf, Holtz, Goodman & Woodward

[57] ABSTRACT

This invention relates to the compounds: N-(mercaptoacy)-cysteine represented by the following formula wherein Z is selected from the group consisting of $CH_3-CH<$, $(CH_3)_2C<$, $(CH_2)_2<$ and $CH_2<$, acting as agents for the liquefaction of sputum, intermediate therefor and a process for manufacture thereof.

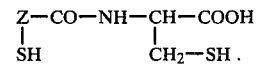

4 Claims, No Drawings

CYSTEINE DERIVATIVES

This invention relates to the novel cysteine derivative, namely N-(mercaptoacyl)-cysteine (I), a process for manufacture of (I), intermediate of (I), namely, N-(benzylmercaptoacyl)-S-benzyl-cysteine (IV) and an agent for the liquefaction of sputum comprising compound (I).

Compound (I) and the intermediate (IV) have not been disclosed in any literature. The compound (I) has, as to be described later, a strong action of decreasing the viscosity of mucus and therefore it is useful as an agent for the liquefaction of sputum. The sulfhydryl compound (I) is considered to liquefy sputum through the splitting of the mucoprotein disulfide linkages.

Compounds of the present invention may be prepared by the following process.

Benzylmercaptoacyl halide represented by the formula (II) reacts with S-benzyl cysteine (III) by a conventional method such as Schotten-Baumann reaction to form N-(benzylmercaptoacyl)-S-benzylcysteine, represented by the formula (IV). The resulting compound (IV) reacts with a reducing agent to allow debenzylation to form N-(mercaptoacyl)-cysteine (I). Any conventional reducing agent may be used, but metallic sodium in liquid ammonia is preferable:

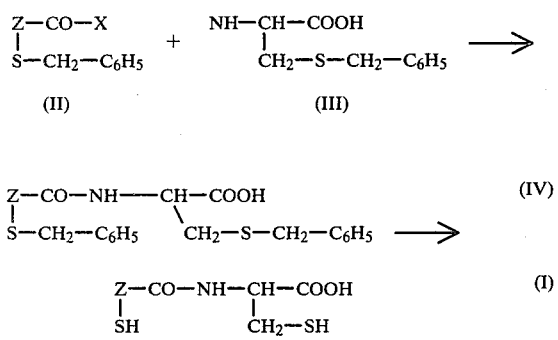

wherein Z is selected from the group consisting of $CH_3-CH<$, $(CH_3)_2C<$, $(CH_2)_2<$ and $CH_2<$ and X is halogen. The compound (II) used in this reaction can be obtained by reacting benzylmercapto carboxylic acid with a halogenizing agent, such as thionyl chloride, by a usual method. Some of the compounds represented by the formula (II) and the formula (III) have an asymmetric carbon atom in their structures and the compound (IV) or (I) obtained therefrom naturally has two asymmetric carbon atoms in each compound. Accordingly, if compounds (II) and/or (III) are optically active substances, compound (IV) or (I) of optically active form is obtained. If either of the two compounds (II) and (III) is an optically active substance, a diastereoisomer is formed. We have obtained two kinds of compounds by reacting the racemic form of the compound (II), wherein Z is $CH_3-CH<$, with the L-form of (III) and the two kinds of compounds obtained are considered to be diastereoisomers, judging from their optical rotations.

The present invention is further illustrated by the following examples and by the pharmacological study in vitro and toxicological study in animals, but they are not to be construed as limiting the present invention.

EXAMPLE 1

(1) Preparation of N-(2-benzylmercaptoisobutyryl)-S-benzyl-L-cysteine (IV, $Z=(CH_3)_2C<$)

73.9 g of S-benzyl-L-cysteine (III) were dissolved in 700 ml of 1 N sodium hydroxide solution. The solution was cooled in an ice bath and stirred. 2-Benzylmercaptoisobutyryl chloride (II, $Z=(CH_3)_2C<$), which was obtained by reacting 63.1 g of 2-benzylmercaptoisobutyric acid with 39.3 g of thionyl chloride, was added dropwise to this solution. The resulting mixture was then stirred for one hour, acidified with hydrochloric acid and extracted with ethyl acetate. The extract was washed with water, dried over sodium sulfate and evaporated to dryness. The residue was chromatographed on silica gel with benzeneethylacetate (1:1) as an eluant. The eluate was evaporated to dryness and an oily residue weighing 46.9 g, representing a yield of 74%, was obtained.

(2) Preparation of N-(2-mercaptoisobutyryl)-L-cysteine (I, $Z=(CH_3)_2C<$)

46.9 g of the compound (IV, $Z=(CH_3)_2C<$) obtained in (1) above were dissolved in 500 ml of liquid ammonia and 21.1 g of metallic sodium were added slowly with stirring. After completion of reaction, 59.4 g of ammonium chloride were added and thereafter the ammonia was removed by distillation. Water was added to the residue to dissolve the solid. The resulting water layer was separated, washed with ethyl acetate, and acidified with hydrochloric acid under cooling. The precipitates thus obtained were extracted with ethyl acetate. The extract was washed with water, dried over sodium sulfate and evaporated to dryness. The product weighed 43.6 g, representing a yield of 88%. After recrystallization from ethyl acetate, the desired compound, melting at 139°–140° C., was obtained.

$[\alpha]_D^{25}$: +32.3° (c=1.0, ethanol).

Anal. Calcd. for $C_7H_{13}NO_3S_2$: C, 37.65; H, 5,87; N, 6.27. Found: C, 37.78; H, 5.86; N, 6.16.

EXAMPLE 2

(1) Preparation of N-(2-benzylmercaptopropionyl)-S-benzyl-L-cysteine-A and -B (IV, $Z=CH_3-CH<$)

211 g of S-benzyl-L-cysteine (III) were dissolved in 22 liter of 0.1 N sodium hydroxide solution, and to the solution 236 g of 2-benzylmercaptopropionyl chloride (II, $Z=CH_3-CH<$) were added dropwise with cooling and stirring. The resulting mixture was then stirred for one hour, acidified with hydrochloric acid and extracted with ethyl acetate. The extract was washed with water, dried over sodium sulfate, and concentrated to form crystals. The crystals were collected by filtration and thereafter washed with a small amount of ethyl acetate. The washed crystals weighed 154 g, representing a yield of 40%. After recrystallization from ethyl acetate, N-(2-benzylmercaptopropionyl)-S-benzyl-L-cysteine-A (IV, $Z=CH_3-CH<$), melting at 111.5°–112.5° C., was obtained.

$[\alpha]_D^{25}$: −135.9° (c=1.4, ethanol).

Anal. Calcd. for $C_{20}H_{23}NO_3S_2$: C, 61.69; H, 5.95; N, 3.60. Found: C, 61.73; H, 5.92; N, 3.62.

The filtrate, from which N-(2-benzylmercaptopropionyl)-S-benzyl-L-cysteine-A was removed, was concentrated and the residue was chromatographed on SiO$_2$ with ethyl acetate. The eluate was evaporated to dryness, and an oily residue weighing 144 g, representing a yield of 37%, was obtained. $[\alpha]_D^{25}$: +46.2° (c=5.2, ethanol). Oily N-(2-benzylmercaptopropionyl)-S-benzyl-L-cysteine-B (IV, Z=CH$_3$CH<) was thus obtained.

(2) (i) Preparation of N-(2-mercaptopropionyl)-L-cysteine-A (I, Z=CH$_3$—CH<)

77.8 g of N-(2-benzylmercaptopropionyl)-S-benzyl-L-cysteine-A were dissolved in 2.5 liter of liquid ammonia. In small portions, 16.1 g of metallic sodium were added with stirring. After completion of reaction, 25 g of ammonium chloride were added and thereafter the ammonia was removed by distillation. Water was added to the residue to dissolve the solid. The resulting water layer was separated, washed with ethyl acetate, and acidified with hydrochloric acid with cooling. The precipitates thus obtained were extracted with ethyl acetate. The extract was washed with water, dried over sodium sulfate, and evaporated to dryness. The product weighed 39.3 g, representing a yield of 94%. After recrystallization from ether, the desired compound, melting at 114°-115° C., was obtained.

$[\alpha]_D^{24}$: +3.5° (c=2.0, ethanol).

Anal. Calcd. for C$_6$H$_{11}$NO$_3$S$_2$: C, 34.45; H, 5.30; N, 6.70. Found: C, 34.95; H, 5.36; N, 6.61.

(2) (ii) Preparation of N-(2-mercaptopropionyl)-L-cysteine-B (I, Z=CH$_3$—CH<)

Proceeding with 144 g of N-(2-benzylmercaptopropionyl)-S-benzyl-L-cysteine-B, 2 liters of liquid ammonia, 28 g of metallic sodium and 37 g of ammonium chloride, according to (2)-(i) above, N-(2-mercaptopropionyl)-L-cysteine-B (I, Z=CH$_3$—CH<) was obtained in a yield of 71 g. (92 percent of the theoretical amount). After recrystallization from ethyl acetate, the desired compound, melting at 124°-125° C., was obtained.

$[\alpha]_D^{24}$: +16.8° (c=1.7, ethanol).

Anal. Calcd. for C$_6$H$_{11}$NO$_3$S$_2$: C, 34.45; H, 5.30; N, 6.70. Found: C, 34.67; H, 5.28; N, 6.77.

EXAMPLE 3

By the methods described in the foregoing examples and using the appropriate starting materials, the following compounds of formula (I) were prepared: N-(3-mercaptopropionyl)-L-cysteine (I, Z=(CH$_2$)$_2$<).

m.p. 97° C. $[\alpha]_D^{25}$: +4.9° (c=1.0, ethanol).

Anal. Calcd. for C$_6$H$_{11}$NO$_3$S$_2$: C, 34.45; H, 5.30; N, 6.70. Found: C, 34.45; H, 5.37; N, 6.70.

N-mercaptoacetyl-L-cysteine (I, Z=CH$_2$<). m.p. 113° C.

(dec.). $[\alpha]_D^{25}$: +24.9° (c=1.0, ethanol).

Anal. Calcd. for C$_5$H$_9$NO$_3$S$_2$: C, 30.77; H, 4.65: N, 7.18. Found: C, 30.80; H, 4.71; N, 7.24.

Mucolytic activity is evaluated by determining the reduction in viscosity of egg white or mucin in vitro. L-Cysteine ethyl ester hydrochloride, L-cysteine methyl ester hydrochloride and acetyl-L-cysteine are used as test compounds for comparison.

(1) In vitro determination of the reduction in viscosity of egg white

Egg white, which is pooled in sufficient quantity to supply material for all the determinations, is gently blended in a mixer for 5 minutes. 9 ml portions of this material are put into a 50-ml beaker and the test solution in a volume of 1 ml containing various concentrations of test compound (test compound is dissolved in distilled water and the solution is adjusted to pH 8.0 with 1 N sodium hydroxide, while distilled water is used as a control) is added. The mixture is then shaken for 20 minutes at 37° C. Viscosity of the resulting solution is determined by an Ostwald viscosimeter. Results shown in Table 1 are percent reduction in relative viscosity at various concentrations of the test compound used.

(2) In vitro determination of the reduction in viscosity of mucin

According to the method presented by Sheffner et al. (Ann. N.Y. Acad. Sci., Vol. 106, P. 298-310, 1963), bacteriological mucin (Nakarai Chemical Co., Ltd.) is dissolved in Sorensen's phosphate buffer (pH=8.0) and a 1% mucin solution is prepared. 0.9 ml portions of the solution are put into test tubes and test compounds (prepared in the same manner as in (1) previously described, except that the buffer solution is used for control) are added to them in a concentration 10 mM. The mixture is then shaken for 1 hour at 37° C. The viscosity of the resulting solution is determined by an Ostwald viscosimeter. Results shown in Table 1 are percent reduction in relative viscosity at 10 mM of the test compounds used.

(3) Changes in the mucolytic activity of the test compounds treated with rabbit serum.

0.1 ml of test compound (prepared in the same manner as (1) previously described) and 0.9 ml of rabbit serum are put into a 50-ml beaker and the resulting mixture is shaken for 30 minutes at 37° C. 9 ml of egg white is then added and it is shaken for another 20 minutes. The viscosity of the resulting solution is determined by an Ostwald viscosimeter. Results shown in Table 2 are percent reduction in the relative viscosity of egg white at 1 mM of the test compounds after treatment with or without rabbit serum.

TABLE 1

| Test compound | Final concentration (mM) | Percent reduction in relative viscosity | |
|---|---|---|---|
| | | egg white | mucin |
| N-(2-mercapto-isobutyryl)-L-cysteine | 0.1 | 23.1 ± 1.4 | |
| | 1.0 | 38.3 ± 2.2 | |
| | 10.0 | 57.0 ± 1.0 | 22.5 ± 1.5 |
| N-(2-mercaptopropionyl)-L-cysteine-A | 0.1 | 24.9 ± 1.5 | |
| | 1.0 | 41.2 ± 2.1 | |
| | 10.0 | 56.4 ± 1.6 | 26.6 ± 1.5 |
| N-(2-mercaptopropionyl)-L-cysteine-B | 0.1 | 24.9 ± 1.4 | |
| | 1.0 | 38.1 ± 2.6 | |
| | 10.0 | 57.7 ± 1.0 | 20.1 ± 0.4 |
| N-(3-mercaptopropionyl)-L-cysteine | 0.1 | 22.8 ± 0.1 | |
| | 1.0 | 36.7 ± 1.6 | |
| | 10.0 | 54.5 ± 4.7 | 28.1 ± 0.5 |
| N-mercapto-acetyl-L-cysteine | 0.1 | 26.1 ± 4.1 | |
| | 1.0 | 39.8 ± 3.0 | |
| | 10.0 | 60.0 ± 4.4 | 31.8 ± 1.5 |
| L-Cysteine ethyl ester hydrochloride | 0.1 | 25.1 ± 3.5 | |
| | 1.0 | 42.0 ± 1.1 | |
| | 10.0 | 59.9 ± 1.2 | 19.7 ± 1.5 |
| L-cysteine methyl ester hydrochloride | 0.1 | 31.1 ± 5.6 | |
| | 1.0 | 45.5 ± 2.0 | |
| | 10.0 | 60.6 ± 2.4 | 17.8 ± 0.2 |
| N-acetyl-L-cysteine | 0.1 | 11.0 ± 2.6 | |
| | 1.0 | 29.5 ± 2.5 | |
| | 10.0 | 49.0 ± 1.8 | 4.8 ± 2.5 |

Results are the mean values ± S.E. of 3 to 5 experiments.

TABLE 2

| Test compound | Final concentration (mM) | Percent reduction in relative viscosity of egg white | | Reduction in the mucolytic activity (%) |
| --- | --- | --- | --- | --- |
| | | untreated with rabbit serum | treated with rabbit serum | |
| N-(2-mercapto-isobutyryl)-L-cysteine | 1.0 | 38.3 ± 2.2 | 32.9 ± 1.0 | 14.1 |
| N-(2-mercapto-propionyl)-L-cysteine-A | 1.0 | 41.2 ± 2.1 | 30.0 ± 1.0 | 27.2 |
| N-(2-mercapto propionyl)-L-cysteine-B | 1.0 | 38.1 ± 2.6 | 31.1 ± 3.8 | 18.8 |
| N-(3-mercapto-propionyl)-L-cysteine | 1.0 | 36.7 ± 1.6 | 38.7 ± 2.6 | −5.4 |
| N-mercapto-acetyl-L-cysteine | 1.0 | 39.8 ± 3.0 | 35.9 ± 0.3 | 9.8 |
| L-cysteine ethyl ester hydrochloride | 1.0 | 42.0 ± 1.1 | 15.4 ± 1.8 | 63.3 |
| L-cysteine methyl ester hydrochloride | 1.0 | 45.5 ± 2.0 | 7.0 ± 1.2 | 84.6 |
| N-acetyl-L-cysteine | 1.0 | 29.5 ± 2.5 | 18.5 ± 0.8 | 37.3 |

Results are the mean values ± S.E. of 3 to 5 experiments.

Toxicological study

Among the compounds (I) of present invention, N-(2-mercaptoisobutyryl)-L-cysteine and N-(2-mercaptopropionyl)-L-cysteine-A well examined with respect to their acute Toxicity. The results are shown in Table 3.

TABLE 3

| Test compound | Animal used | Route of administration | Acute Toxicity ($LD_{50}$) |
| --- | --- | --- | --- |
| N-(2-mercapto-isobutyryl)-L-cysteine | mouse | i.p. | 2285 mg/kg |
| | | i.v. | 989.6 mg/kg |
| N-(2-mercapto-propionyl)-L-cysteine-A | mouse | i.p. | 2092 mg/kg |

Animal used 5-week-old male mice of ddy strain (body weight 24–28 g) are used. They are fed for one week before experiment and animals exhibiting abnormal growth during this period are excluded.

Test solution

Test compound is added to physiological saline and the resulting solution is neutralized with sodium hydroxide to form a 5% solution (pH 7.0).

Observation

After administration of test solution, general symptoms and deaths which are caused during seven days are observed. The $LD_{50}$ values are calculated according to the method of Litchfield and Wilcoxon.

As evident from the pharmacological study and the toxicological study the compound (I) of this invention is useful as an agent for the liquefaction of sputum. In the case of medical treatment of an adult, the dose per day ranges 100–600 mg depending upon the method and the frequency of administration. The compound may be administered orally or directly to trachea, or inhaled in aerosol form.

A medicinal composition of the compound of this invention may be processed for oral administration, into tablets, powder or encapsulated form so that it is easily absorbed from the stomach or intestines, and it may be processed into such form in view of convenience. For this purpose, a binding agent such as gelatin, sorbitol, polyvinyl pyrrolidone; a forming agent such as lactose, a starch, calcium phosphate; a lubricating agent such as magnesium stearate, talc; a collapsing agent such as carboxy methyl cellulose calcium, may be added. The composition may be processed into an aqueous solution of the compound alone or its salt such as sodium salt, for the use of aerosol or for injection use.

Following are examples of formulations in which N-(2-mercaptoisobutyryl)-L-cysteine is used as a model but said compound may be replaced by other compounds of formula (I) in accordance with forms processed.

(1) For oral administration

| (a) Tablet form | |
| --- | --- |
| N-2-mercaptoisobutyryl)-L-cysteine | 100 mg |
| Ethyl cellulose | 50 mg |
| Crystalline cellulose | 80 mg |
| Carboxymethyl cellulose | 7 mg |
| Magnesium stearate | 3 mg |
| Total | 240 mg |

Tablet may be coated with film-coating which is usually adopted. It may be coated further with a sugar-coating.

| (b) Granular form | |
| --- | --- |
| N-(2-mercaptoisobutyryl)-L-cysteine | 100 mg |
| Polyvinyl pyrrolidone | 25 mg |
| Lactose | 365 mg |
| Talc | 10 mg |
| Total | 500 mg |
| (c) Powder form | |
| N-(2-mercaptoisobutyryl)-L-cysteine | 100 mg |
| Lactose | 500 mg |
| Starch | 370 mg |
| Colloidal silica | 30 mg |
| Total | 1000 mg |
| (d) Encapsulated form | |
| N-(2-mercaptoisobutyryl)-L-cysteine | 100 mg |
| Lactose | 32 mg |
| Crystalline cellulose | 56 mg |
| Colloidal silica | 2 mg |
| Total | 190 mg |

(2) Aerosol form and injection form 250 mg of N-(2-mercaptoisobutyryl)-L-cysteine are contained in 5 ml of an aqueous solution of pH 6.5–7.0, as the sodium salt form of the compound.

What is claimed is:
1. N-(2-mercaptoisobutyryl)-cysteine.
2. N-(2-mercaptopropionyl)-cysteine.
3. A composition for the liquefaction of sputum containing an effective amount of the N-(mercaptoacyl)-cysteine having the formula

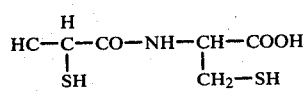
and a medicinal carrier.
4. A composition for the liquefaction of sputum containing an effective amount of the N-(mercaptoacyl)-cysteine having the formula
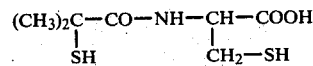
and a medicinal carrier.
* * * * *